United States Patent [19]

Jones et al.

[11] 4,361,053

[45] Nov. 30, 1982

[54] MOLTEN METAL BATH TEMPERATURE SENSOR AND SAMPLER

[75] Inventors: Gregory W. Jones, Jenkintown; L. Raymond Jones, Jr., Huntingdon Valley, both of Pa.

[73] Assignee: Electro-Nite Co., Philadelphia, Pa.

[21] Appl. No.: 206,214

[22] Filed: Nov. 13, 1980

[51] Int. Cl.³ .............................................. G01N 1/10
[52] U.S. Cl. ..................................................... 73/864.53
[58] Field of Search ......... 73/DIG. 9, 864.53, 864.58, 73/863.11

[56] References Cited

U.S. PATENT DOCUMENTS 3,221,559 12/1965 Miller, Jr. et al. ................. 73/425.4
3,824,837 7/1974 Nagaoka et al. ................... 73/17 R
3,994,172 11/1976 Kelsey ............................... 73/425.4
4,002,069 1/1977 Takemura et al. ............. 73/DIG. 9

Primary Examiner—Jerry W. Myracle
Attorney, Agent, or Firm—Seidel, Gonda, Goldhammer & Panitch

[57] ABSTRACT

The sampler includes two refractory body sections with two metal plates extending between and interconnecting the sections into a rigid unit. Said metal plates define two walls of a sampling chamber. Refractory surfaces define the remaining walls of said chamber. A first thermocouple is provided in the chamber for sensing the liquidus temperature as the sample cools and a second thermocouple senses bath temperature.

14 Claims, 5 Drawing Figures

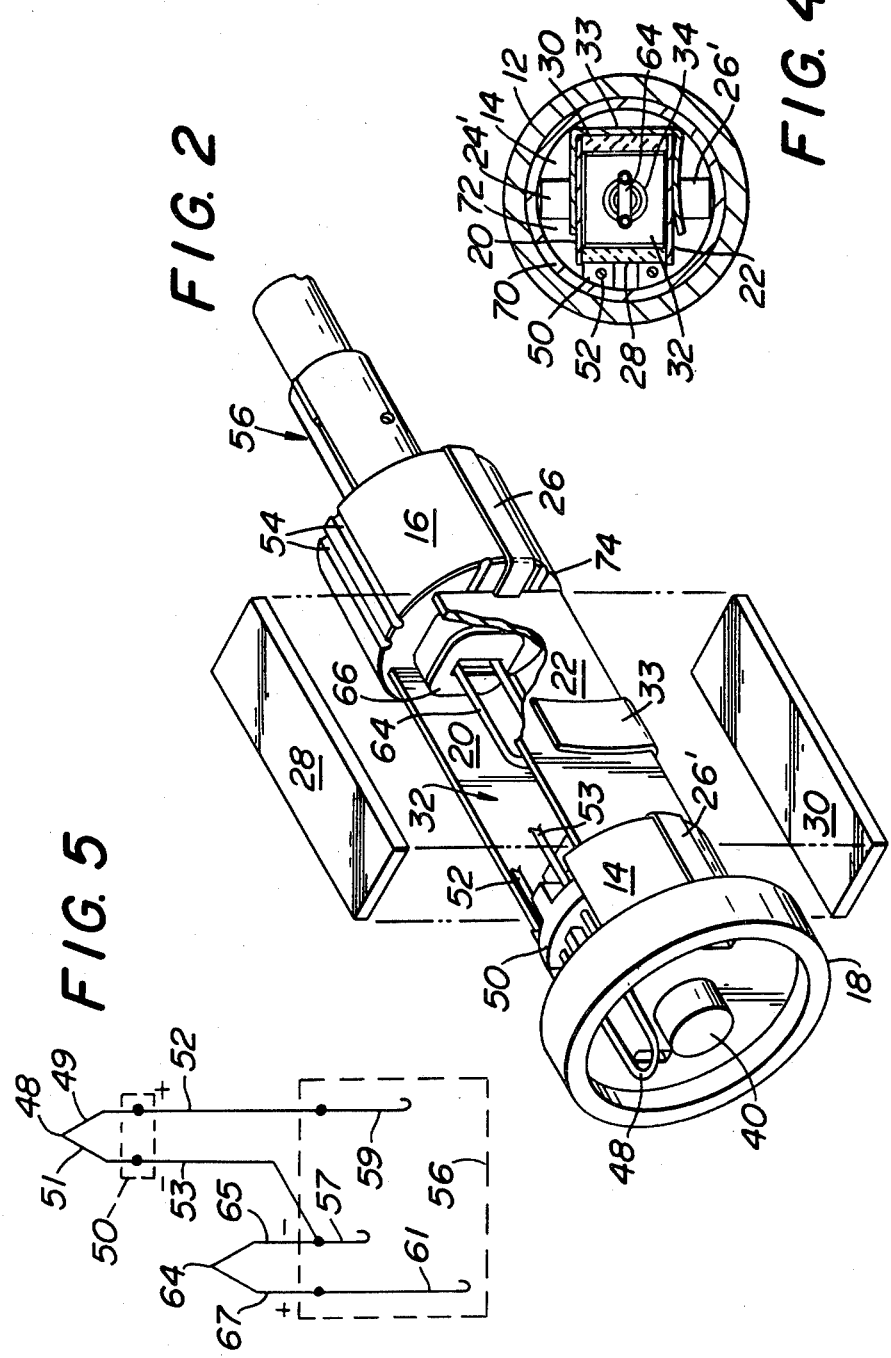

MOLTEN METAL BATH TEMPERATURE SENSOR AND SAMPLER

BACKGROUND

Molten metal samplers generally provide a metal or refractory body having a chamber for immersion below surface level to obtain a sample of molten metal such as steel. The body is generally provided with some type of inlet to facilitate entry of the molten metal into the chamber. It is known to define the chamber in a manner so as to have two metal plates oppositely disposed and cooperating with a hole in a refractory body therebetween. A chamber defined in this manner provides a balance between the heat conducting characteristics of the metal plates and the refractory body whereby the sample solidifies at a satisfactory rate. When the walls of the sampling chamber are defined solely by refractory, the sample cools slowly and starts to segregate. When the walls of the chamber are defined solely by metal plates, the sample cools too quickly. When the sample cools too quickly, the liquidus temperature which is known to define sample carbon passes through the arrest zone too quickly to provide a discernible reading.

When the walls of the chamber are defined by a ceramic, the specimen has an irregular surface and hence must first be machined on a grinding machine to provide smooth surfaces before being tested. By using metal plates for opposite walls of the chamber, the specimen will have smooth opposite surfaces whereby the grinding step may be eliminated or minimized and the specimen may be analyzed directly on a spectrometer.

The problem solved by the present invention is how to structurally interrelate compounds of a molten metal sampler so as to obtain a desired rate of solidification of the sample while at the same time provide a sampler which can be made economically on a production line basis.

SUMMARY OF THE INVENTION

The present invention is directed to a molten metal sampling apparatus. The apparatus includes a body made in two separate sections from a refractory. At least one metal plate is utilized to rigidly interconnect the body sections and to also define at least one wall of a sampling chamber. Another wall of the sampling chamber is defined by a refractory surface. Entry is provided into the chamber.

The sampling apparatus is preferably constructed in a manner so as to have a temperature sensing element within the sampling chamber for sensing the liquidus arrest temperature. The sampling apparatus is preferably also constructed so as to include a temperature sensing element positioned to sense the temperature of the bath.

It is an object of the present invention to provide a molten metal sampler which is constructed in a manner to provide a desired control of solidification of a sample while at the same time is constructed in a manner so as to facilitate a reliable sampler capable of being made on a production line basis.

It is another object of the present invention to provide a molten metal sampler having a plurality of variables which facilitate obtaining reliability of results.

Other objects will appear hereinafter.

For the purposes of illustrating the invention, there is shown in the drawings a form which is presently preferred; it being understood, however, that this invention is not limited to the precise arrangements and instrumentalities shown.

FIG. 2 is an exploded perspective view.

FIG. 4 is a sectional view taken along the line 4—4 in FIG. 1.

FIG. 5 is a wiring diagram for the thermocouples.

DETAILED DESCRIPTION

Figure 1:
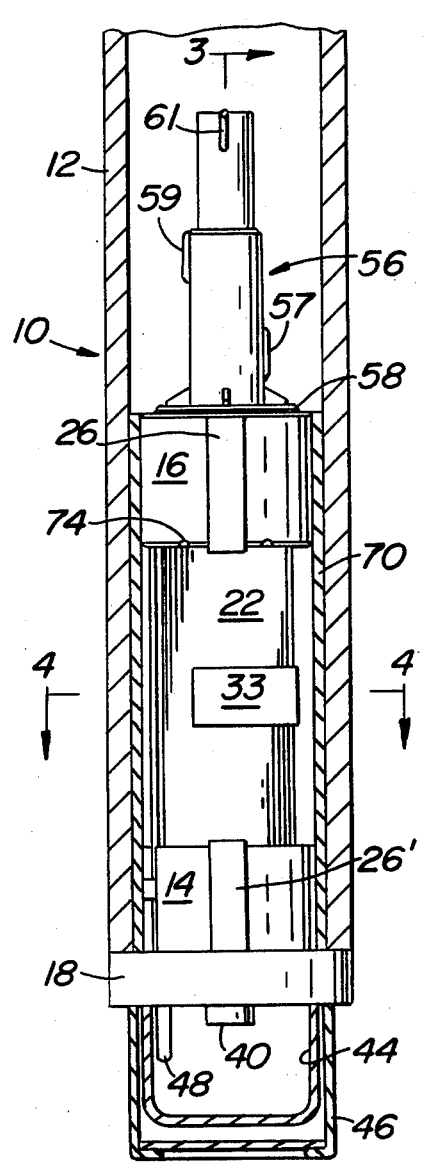
FIG. 1 is a vertical sectional view through the immersion end of a sampler in accordance with the present invention.

Referring to the drawing in detail, wherein like numerals indicate like elements, there is shown in FIG. 1 a molten metal sampler in accordance with the present invention designated generally as 10. The sampler 10 is adapted to be immersed below liquid level in a bath of molten metal such as steel. The sampler 10 includes a tube 12 made from an expendible material such as paper. Within the immersion end of the tube 12, there is provided a first body section 14 and a second body section 16. The body sections 14 and 16 are preferably made from a heat insulating refractory such as ceramic.

The body sections 14 and 16 perform different functions. Each body section is molded to the minimum size needed in order to perform its function. Body section 14 is provided with a radially outwardly directed flange 18 for contact with an endface of the tube 12. The body sections 14 and 16 are rigidly interconnected for manipulation as a unit by way of first and second plates 20, 22. The plates 20 and 22 are metal plates made from a material such as carbon steel. The plates 20 and 22 preferably have a thickness in the range of 0.04 to 0.06 inches when the volume of the sample is approximately 0.5 cubic inches. With a sample of that size, it has been found that low carbon steel plates having a thickness of less than about 0.04 inches weld to the sample and if the plates have a thickness greater than 0.06 inches, they chill the sample too quickly.

Plate 20 has an extension 24 at one end. Plate 22 has an extension 26 at one end. The extensions 24 and 26 are opposite one another and include a C-shaped portion so as to embrace oppositely disposed radial surfaces on the body section 16. Similar extensions designated 24' and 26' embrace similar surfaces on the body section 14. The terminal ends on the extensions 24' and 26' extend radially inwardly through slots adjacent to the flange 18. The plates 20, 22 rigidly interconnect the body sections 14 and 16 in a manner whereby they cannot rotate relative to one another or move inwardly or outwardly away from one another. Each of the extensions 24, 26, 24' and 26' fits into an axially extending groove on the outer periphery of its associated body section.

Figure 3:
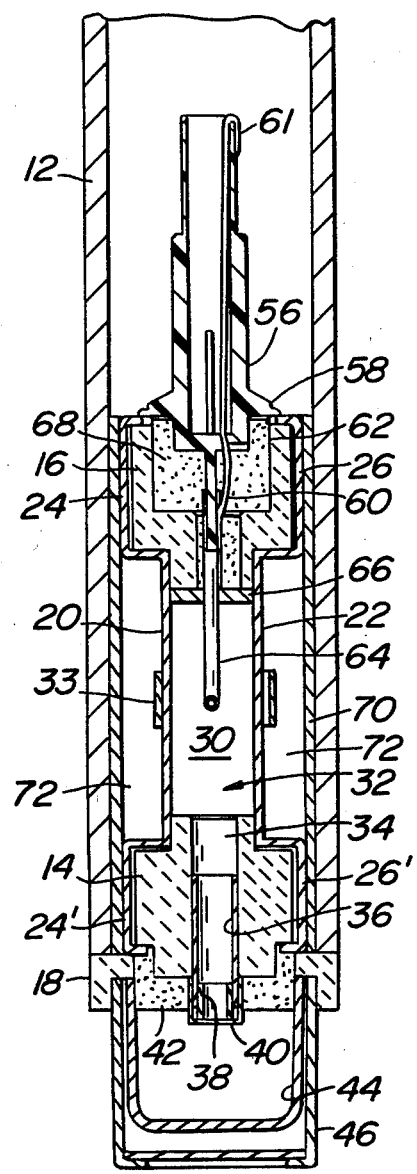
FIG. 3 is a sectional view taken along the line 3—3 in FIG. 1.

The plates 20, 22 are preferably disposed opposite one another so as to define opposite faces of the sampling chamber 32. The sampling chamber 32 is preferably rectangular in section as shown more clearly in FIG. 4. Each of the two remaining opposite faces of the sampling chamber 32 is defined by a flat heat insulating refractory plate 28, 30. Plates 28 and 30 are thicker than the plates 20, 22 and preferably have a thickness of about 0.125 inches. A U-shaped clip 33 made from spring steel embraces the plates 20, 22 and the plate 30 while applying sufficient pressure to the plates 20, 22 so as to hold the plate 28 therebetween. As shown in FIGS. 2 and 3, each of the body sections 14 and 16 has an axially extending boss which is rectangular in section. Each of the plates 20, 22, 28 and 30 is in contact with one of the faces of the bosses on the body sections 14, 16. This feature facilitates rapid assembly and provides for quality control in uniformity of the size of the sampling chamber 32.

The body section 14 is preferably provided with an axial bore 34 which is an entry passage into the sampling chamber 32. However, the entry to chamber 32 can be radially disposed in a manner well known in the sampling art. Bore 34 is provided with a metal liner 36. Within liner 36 there is provided an aluminum sleeve 38. Sleeve 38 is preferably made from aluminum or equivalent so as to kill the sample. A cap 40 is preferably provided for the exposed portion of the liner 36 so as to prevent the entry of foreign matter into the bore 34 during the manufacturing process.

A refractory cement 42 is applied to the end face of body section 14 so as to coincide with the end face of the axially extending portion of the flange 18. The level of refractory cement 42 is slightly below the closed end of the cap 40. Thereafter, an expendible metal cap 44 and an expendible paper cap 46 are introduced into the refractory cement 42 before it cures. A bath temperature sensing element such as thermocouple 48 is supported by the body section 14. The thermocouple 48 has a support 50 disposed within an axially extending peripheral slot. See FIG. 2.

Leg 49 of thermocouple 48 terminates at lead wire 52. The other leg 51 of thermocouple 48 terminates at lead wire 53. Lead wires 52, 53 are conductors which extend from the thermocouple 48 through grooves 54 on the outer peripheral surface of body section 16, to connector 56. Conductor 52 terminates at bare wire contact 59 on connector 56. Conductor 53 terminates at bare wire contact 57 on connector 56. Leg 65 of thermocouple 64 terminates at bare wire contact 57 on connector 56 also. The other leg 67 of thermocouple 64 terminates at bare wire contact 61. Connector 56 will facilitate coupling the sampler to a temperature recorder in all the rotative positions of the connector 56 which is a nondirectional connector. Connector 56 is preferably made from a material which is electrically non-conductive such as plastic.

The connector 56 has a radially outwardly directed flange 58 overlying an end face of the body section 16. The last mentioned end face of body section 16 has an axially positioned cavity 62. The cavity 62 is filled with refractory cement 68. Connector 56 has an integral extension 60 which extends through the cavity 62 and into a centrally arranged bore for supporting a temperature sensing element such as thermocouple 64. Thermocouple 64 has its hot junction along the longitudinal axis of the sampling chamber 32 and preferably such hot junction is approximately equidistant from the ends of the sampling chamber 32. The upper end of the sampling chamber 32 is defined by metal chill plate 66 having a hole through which the legs of the thermocouple 64 extend.

A paper tube 70 is telescoped over the body sections 14 and 16 with a force fit or with adhesive therebetween. As shown more clearly in FIG. 4, the walls defining the sampling chamber 32 cooperate with the inner surface of the tube 70 to define generally crescent-shaped air spaces 72. The air spaces 72 communicate with the chamber 32 by way of grooves 74 on the end face of the body section 16. See FIGS. 1 and 2. Tube 70 has a force-fit with the inner surface of tube 12 or is adhesively bonded thereto to prevent the assembled unit from falling out the open end of tube 12.

ASSEMBLY OF THE SAMPLER

The body sections 14 and 16 are molded from a refractory material. Subassemblies are provided by adding the liner 36, sleeve 38 and cap 40 to the body section 14. Thermocouple 48 is attached to lead wires 52, 53 and thermocouple 64 is attached to lead wires 65, 67. The thermocouple extension leads are attached to connector 56 to provide the bare wire contacts 57, 59 and 61. The connector 56 and the thermocouple 64 are preassembled with respect to the body 16 while leaving space so that the cement 68 may be added. Thereafter, the connector 56 is pressed so as to cause flange 58 to engage the end face of the body section 16 thereby orientating the thermocouple 64 in the proper location. Chill plate 66 is positioned and bonded to the boss on the body section 16.

Plates 20 and 22 are positioned and their terminal ends bent so as to overlie the end face of the body section 16 as shown in FIG. 3. The bent ends on extensions 24' and 26' are inserted into the slots of body section 14. The plates 20, 22 rigidly interconnect the body sections 14 and 16. The refractory plates 28 and 30 are positioned to enclose the sampling chamber 32. Thereafter, the spring clip 33 is applied. Cement 42 is applied and caps 44, 46 are inserted into the cement 42 while it is still uncured. Thereafter, the paper tube 70 is telescoped over the unit. Then tube 70 is telescoped into tube 12.

METHOD OF USE

Connector 56 is connected to contacts on a pole in a conventional manner with tube 12 telescoped over the pole. The pole is manipulated so that one end as shown in the drawings is immersed below liquid metal level. Paper cap 46 is consumed by the bath. Cap 44 protects the thermocouple 48 while passing through any slag on the bath. In doing so, the cap 44 is consumed by the bath. Thermocouple 48 senses the temperature of the bath. Cap 40 is consumed and a sample enters the chamber 32. The sample is killed and partially chilled as it passes through the liner 36 by melting the aluminum sleeve 38.

As the sample enters the chamber 32, the air or other gasses within chamber 32 are forced through the grooves 74 into the air spaces 72. The sample enters the entire chamber 32 and is chilled at its upper end by contact with the plate 66. The sample is cooled on two sides by the metal plates 20, 22 and on two sides by the refractory surfaces of the plates 28, 30. When the sample is removed, it will be rectangular in cross section with two smooth surfaces for analysis by a spectrometer.

The desired control rate of solidification of the sample so as to have a distinct liquidus temperature arrest measured by the thermocouple 64 is variable by changing the thickness of the plates 20, 22 and 28, 30. Another control is attained by the size of the grooves 74 which control the rate in which air exits from the chamber 32. Another control is to vary the length of the metal liner 36 which will control the rate of chill of the sample as it enters the chamber 32. In a typical embodiment wherein the chamber 32 has a length of 1.5 inches, liner 36 may have a length of 0.875 inches and an inner diameter of 0.25 inches.

The chill plate 66 protects the unfired refractory cement 68 from any substantial direct contact with the sample. Direct contact between unfired cement and a metal sample generates gasses which interferes with the homogeneity of the sample. Also, the chill plate 66 causes the sample to solidify faster at the top end where there is a tendency to obtain voids in the sample.

The body sections 14 and 16 are preferably made from non-metallic heat resistant castable body which is preferably a ceramic. One such material which is commercially available is sold under the trademark Cordirite. The body sections 14 and 16 are of a minimum size in order to perform their intended function whereby a minimum amount of material is utilized. The plates 20, 22 perform the dual function of rigidly interconnecting the body sections 14 and 16 while defining at least one and preferably two sides of the sampling chamber 32.

The present invention may be embodied in other specific forms without departing from the spirit or essential attributes thereof and, accordingly, reference should be made to the appended claims, rather than to the foregoing specification, as indicating the scope of the invention.

We claim:

1. Molten metal sampling apparatus comprising a body have two sections, means rigidly interconnecting said sections, said means including two metal plates arranged to define opposite side walls of a sampling chamber located between said sections with two remaining walls of said sampling chamber being defined by flat refractory plates, and means defining an entry into said chamber.

2. Apparatus in accordance with claim 1 wherein said body sections have rectangular bosses extending towards each other, said bosses corresponding generally to the transverse dimensions of the sampling chamber, each plate being in contact with one surface on each boss.

3. Apparatus in accordance with claim 1 wherein said chamber has a volume of about 0.5 in.$^3$ and said metal plates have a thickness of 0.04 to 0.06 inches.

4. Molten metal sampling apparatus comprising a body having two sections, means rigidly interconnecting said sections, said means including at least one metal plate which also defines at least one wall of a sampling chamber located between said sections, another wall of said sampling chamber being defined by a refractory surface, a temperature sensing element within said sampling chamber and supported by one of said body sections, said temperature sensing element extending through a hole in a chill plate positioned to constitute one end wall of the sampling chamber, and means defining an entry into said chamber.

5. A sampler in accordance with claim 4 wherein the other body section is provided with said means defining an entry into said chamber, the sensing portion of said temperature sensing element and said entry being generally coaxial with said chamber.

6. Apparatus comprising a support having an immersion end, a molten metal sampler supported by said immersion end, said sampler including two body sections, two metal plates extending between and interconnecting said sections into a rigid unit, intermediate portions of said plates defining two walls of a sampling chamber, refractory surfaces defining the remaining walls of said chamber, means defining an inlet to said chamber, and a temperature sensing unit within said chamber with its temperature sensing portion being generally along the center line of said chamber.

7. Apparatus in accordance with claim 6 including means for sensing a temperature of a bath and supported by one of said body sections.

8. Molten metal sampling apparatus comprising first and second spaced body sections each having a portion which is cylindrical, each body section having a rectangular boss, said bosses extending towards each other, a plurality of plates, each plate having its opposite ends overlying one surface on said bosses, said plates cooperating to form a rectangular sampling chamber, means to facilitate discharge of gasses from said sampling chamber as a sample of molten metal enters the chamber, and means defining an entry into said sampling chamber.

9. Apparatus in accordance with claim 8 wherein two of said plates are metal plates and the remaining plates are flat plates made from a heat insulating refractory material.

10. Molten metal sampling apparatus comprising a support tube having an immersion end, a sampler supported by said immersion end of said tube, said sampler including at least one refractory body and a sampling chamber, an entry passage for permitting a molten sample to enter said chamber, said passage being coaxial with said tube, means for permitting discharge of gasses from within said chamber as said chamber becomes filled with molten metal, a thermocouple within said chamber and having its hot junction generally along the longitudinal axis of the chamber, said chamber being rectangular in section, oppositely disposed walls of said chamber being metal plates having a thickness sufficiently great with respect to the volume of the sample so that the metal plates do not weld to the sample as the sample cools, a chill plate defining an end of the chamber remote from said entry into the chamber, said chill plate having a hole through which legs of the thermocouple extend, an electrical connector coupled to said thermocouple.

11. Apparatus in accordance with claim 10 wherein each metal plate has a radially disposed end portion for rigidly interconnecting discrete sections of the body in a predetermined spaced relationship so that the sampling chamber is disposed between said bodies.

12. Apparatus in accordance with claim 10 wherein said means for discharge of gasses includes at least one air space between said chamber and said tube inner surface, pasage means providing communication between one end of said chamber and said air space.

13. Apparatus in accordance with claim 10 including temperature sensing means for sensing bath temperature.

14. Apparatus in accordance with claim 10 including a chill sleeve in said entry passage for partially chilling a sample before it enters said chamber.

* * * * *